United States Patent
Shin et al.

(10) Patent No.: US 9,365,594 B2
(45) Date of Patent: Jun. 14, 2016

(54) ENHANCED SUBSTANTIVITY OF COSMETIC INGREDIENTS ON KERATINOUS SUBSTRATE

(71) Applicant: Avon Products, Inc., Suffern, NY (US)

(72) Inventors: Sung Bin Shin, Mahway, NJ (US); Sen Yang, Nanuet, NY (US)

(73) Assignee: Avon Products, Inc., New York, NY (US)

( * ) Notice: Subject to any disclaimer, the term of this patent is extended or adjusted under 35 U.S.C. 154(b) by 178 days.

(21) Appl. No.: 13/717,920

(22) Filed: Dec. 18, 2012

(65) Prior Publication Data

US 2014/0170097 A1    Jun. 19, 2014

(51) Int. Cl.
- *A61K 8/02* (2006.01)
- *C07F 7/08* (2006.01)
- *C07F 7/18* (2006.01)

(52) U.S. Cl.
CPC .............. *C07F 7/0801* (2013.01); *C07F 7/1836* (2013.01); *C07F 7/1876* (2013.01); *Y10T 428/2982* (2015.01)

(58) Field of Classification Search
None
See application file for complete search history.

(56) References Cited

U.S. PATENT DOCUMENTS

| | | |
|---|---|---|
| 6,239,088 B1 | 5/2001 | George et al. |
| 2010/0152473 A1 | 6/2010 | Yanagisawa |
| 2012/0110752 A1 | 5/2012 | Lamberty et al. |

FOREIGN PATENT DOCUMENTS

| | | | |
|---|---|---|---|
| KR | 2008076260 A | 8/2008 | |
| WO | 2008/148809 A1 | 12/2008 | |
| WO | WO2012061025 A1 * | 5/2012 | ............ A61Q 5/10 |

OTHER PUBLICATIONS

Haruka Fukushima et al., Surface-initiated enzymatic vinyl polymerization: synthesis of polymer-grafted silica particles using horseradish peroxidase as catalyst, Mar. 12, 2012, Polymer Chemisty, vol. 3, pp. 1123-1125.*

* cited by examiner

*Primary Examiner* — Nannette Holloman
(74) *Attorney, Agent, or Firm* — David M. Joyal; Joan M McGillycoddy

(57) ABSTRACT

The invention provides compositions and methods for reversible covalent binding of benefit agents to keratinous substrates through the reaction of a dicarbonyl functional group on the surface of a benefit agent with reactive amines on keratinous surfaces. The deposits formed are durable and resistant to transfer, but are readily removed by contacting the deposit with an amine-containing solution.

20 Claims, 1 Drawing Sheet

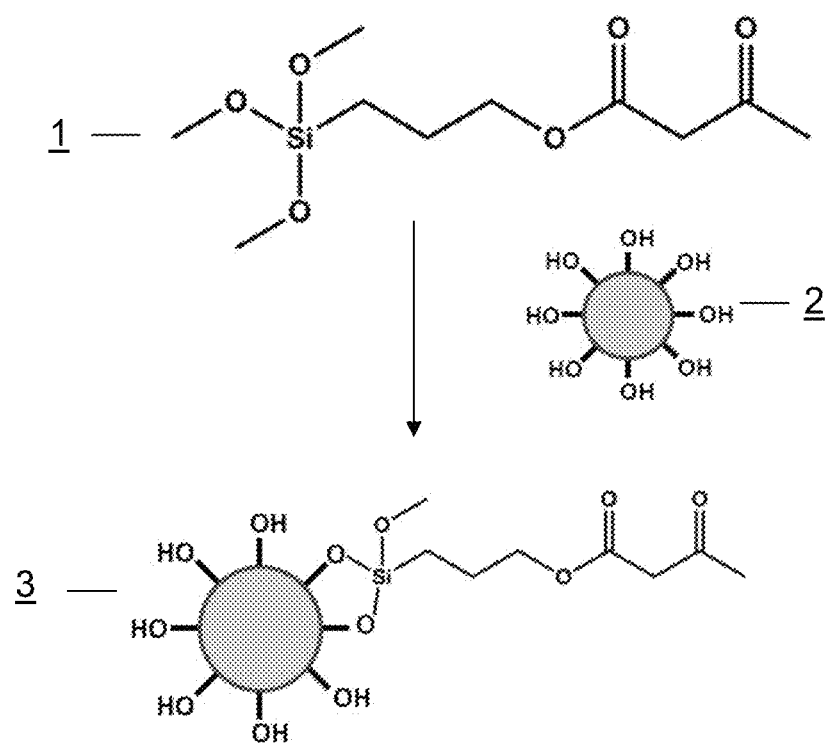

ENHANCED SUBSTANTIVITY OF COSMETIC INGREDIENTS ON KERATINOUS SUBSTRATE

FIELD OF INVENTION

The present invention provides compositions and methods for forming durable deposits on keratinous substrates via covalent binding of benefit agents to keratinous substrates. More particularly, the present invention relates to compositions including a functionalized benefit agent having a diketo moiety for adhering the benefit agent to a keratinous substrate via a covalent bond.

BACKGROUND OF THE INVENTION

Currently available cosmetic compositions that are applied to the skin or lips, including, for example, foundations and lipsticks have a tendency to migrate or transfer from the surface to which they are applied onto a substrate that comes into contact, leading to an unpleasant appearance around the lips and the eyes, which particularly makes wrinkles and fine lines more prominent. This migration is often identified by consumers as being a major defect of, for example, conventional lipsticks, foundations, concealer products and eye make-ups. In addition, these compositions generally are not long-lasting, leading to modifications of the color which generally follow an interaction with the sebum and sweat secreted by the skin, or with saliva on the lips. The resulting smearing or migration leads to an uneven coating and uneven color, requiring the user to reapply the cosmetic frequently.

In one aspect, the invention provides compositions and methods for covalent binding of benefit agents to keratinous substrates, Efforts to improve the durability and transfer resistance of cosmetic color products have focused on the use of polymeric film formers. However, many of these film forming compositions suffer from pressure sensitive tackiness and lack sufficient flexibility. Discomfort of having the added film layer is a large complaint among the users of current long-wear cosmetic products in the market.

There remains a technology gap in providing a non-transfer, long-lasting cosmetic composition, which is also comfortable to consumers over long periods of wear time.

The present invention, however, reduces the need for the film layer by providing a reversible covalent attachment of cosmetic ingredient (i.e., benefit agent) to skin and hair surfaces, which makes the film-former unnecessary and provides stronger adhesion than the prior art. The cosmetic ingredient is thereby physically attached to the skin surface and substantivity is dramatically enhanced.

Although covalently linking pigment to the skin is one approach to achieving transfer resistant cosmetic pigment, reversible attachment of various skin benefit agents has not been described. There is a continuing need in the art for cosmetics that impart desired attributes such as long-wear, transfer resistance, and comfort to the integuments to which the cosmetic is applied.

It is therefore an object of the invention to provide improved cosmetic and personal care products having functionalized skin benefit agents which reversibly adhere to keratinous substrates that are long-wearing yet comfortable and which, when used in a pigmented or colored composition, reduces the tendency of the color to migrate from the surface.

SUMMARY OF THE INVENTION

In accordance with the foregoing objectives and others detailed herein, the invention overcomes deficiencies associated with the prior art by providing compositions and methods for forming durable deposits on keratinous substrates.

In one aspect, the invention provides compositions and methods for covalent binding of benefit agents to keratinous substrates, such as skin, nails and hair which can be reversed when desired. Unlike conventional topically applied benefit agents, such as colorants or sunscreen agents, the covalently adhered benefit agents according to the present invention will not readily wear off or transfer. The invention provides a topical application of a benefit agent having long-lasting substantivity, i.e., continuing therapeutic or cosmetic action despite removal or evaporation of the vehicle, contact with surfaces (e.g., napkins) or interaction with sweat and sebum.

Desirable characteristics of the resulting covalently adhered film formed by the compositions include without limitation: good application, the production of a uniform film of desired sheen or gloss, rapid drying time, good adhesion, transfer resistance, ease of removal, flexibility, comfort and/or good film strength to avoid cracking and flaking of the film, preferably in the absence of irritation of the skin, hair, and/or nails or other keratinous surfaces upon which the film-forming composition is applied.

In one aspect, the invention provides compounds for reversibly adhering a benefit agent to keratinous substrates, such as skin, lips, nails and/or hair, having the structure of Formula I and cosmetically suitable salts thereof:

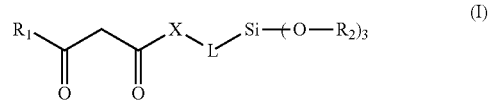

(I)

wherein $R_1$ is hydrogen or a $C_1$-$C_{20}$ hydrocarbon optionally substituted with 1-12 heteroatoms selected from oxygen, nitrogen, sulfur and halogen (e.g., Cl, F, Br, I etc.). Preferably, $R_1$ is a lower alkyl (e.g., $R_1$ is methyl, ethyl, propyl, butyl, pentyl or hexyl groups) and more preferred still, $R_1$ is methyl;

$R_2$ is independently selected at each occurrence from $C_1$-$C_7$ hydrocarbon optionally substituted with 1-4 heteroatoms selected from oxygen, nitrogen, sulfur and halogen (e.g., Cl, F, Br, I etc.). Preferably, $R_2$ is selected from among methyl, ethyl, propyl, butyl, pentyl, hexyl, phenyl or benzyl. More preferably, $R_2$ ethyl and/or methyl. Most preferably, $R_2$ is methyl;

X is a bond (i.e., X is absent), —O—, —NR$^N$—, —S—; wherein y and z are independently an integer from 1 to 10, (preferably from 1 to 5, more preferably 1-3);

L is a group of the form —$X_1$—(CR*$_2$)$_n$—$X_2$—(CR*$_2$)$_m$—$X_3$—; wherein $X_1$, $X_2$, and $X_3$ are independently at each occurrence a bond, —O—, —NR$^N$—, —S—, —(OCH$_2$CH$_2$)$_y$—, or —(CH$_2$CH$_2$O)$_z$—, wherein y and z are independently an integer from 1 to 10 (preferably from 1 to 3), and n and m are independently an integer from 0 to 10 (preferably from 1 to 3);

$R^N$ is independently at each occurrence hydrogen, lower alkyl (i.e., $C_1$-$C_6$ alkyl, such as, ethyl, ethyl, propyl, butyl, pentyl or hexyl), phenyl, benzyl, or the like, and is most typically methyl.

R* is independently selected at each occurrence from H, $C_1$-$C_4$ alkyl (e.g., methyl, ethyl, propyl or butyl) or halogen (e.g., Cl, F, Br, I etc.) and is most typically methyl or hydrogen.

The benefit agent is typically in particulate form, and may have a median particle size (measured on a volume basis) greater than about 5 nm. The particulate may have a median particle size ranging from about 10 nm up to about 100 microns or even larger, typically, from about 10 nm to about 100 nm, or about 100 nm to about 10 microns, or about 10 microns to about 20 microns, or about 20 microns to about 50 microns, or larger. Examples include, without limitation, inorganic and organic pigments and pearls, fillers and powders. Notable inorganic pigments include without limitation silica and metal oxides such as iron oxide, titanium oxide and zinc oxide. Alternatively, the benefit agent may not be in particulate form and instead may be an organic molecule (e.g., an organic dye, steroid, drug, or other small molecule) or biomolecule (e.g., oligopeptides, polypeptides, cholesterol, polysaccharides, etc.) or the like.

In one embodiment, the compounds for reversibly adhering a benefit agent to keratinous substrates have the structure of Formula Ic:

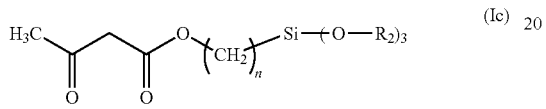

wherein $R_2$ is independently selected at each occurrence from $C_1$-$C_7$ hydrocarbon optionally substituted with 1-4 heteroatoms selected from oxygen, nitrogen, sulfur and halogen (e.g., Cl, F, Br, I etc.). Preferably, $R_2$ is selected from among methyl, ethyl, propyl, butyl, pentyl, hexyl, phenyl or benzyl. More preferably, $R_2$ ethyl and/or methyl. Most preferably, $R_2$ is methyl.

In another aspect of the invention, methods of forming a functionalized benefit agent for reversibly adhering a benefit agent to a keratinous surface are provided. Typically the method will involve reacting a benefit agent having one or more hydroxyl groups with any of the compounds for reversibly adhering a benefit agent to keratinous substrates described herein, including those of Formula I-Id.

Another aspect of the invention provides pigments surface functionalized with a beta dicarbonyl compound including, without limitation, those of Formula I-Id. Preferably, the beta dicarbonyl compound is a beta diketo-ester. More preferably, the beta diketo-ester is covalently attached to the surface of the pigment through a siloxane linkage.

In another aspect of the invention, surface functionalized pigments for reversibly adhering a benefit agent to keratinous substrates are provided, wherein the surface functionalized pigment is a reaction product of any of the compounds for reversibly adhering a benefit agent to keratinous substrates described herein, including those of Formula I-Id, and an inorganic oxide particle (e.g., silica or metal oxides where the metal is preferably selected from among magnesium, calcium, aluminum, iron, titanium, zirconium, chromium, manganese, cobalt, cerium, nickel, zinc and composites and mixtures thereof).

In one aspect, the invention provides cosmetic compositions comprising a surface functionalized pigment for reversibly adhering a benefit agent to keratinous substrates and a cosmetically acceptable vehicle, where the surface functionalized pigment is a reaction product of any of the compounds for reversibly adhering a benefit agent to keratinous substrates described herein, including those of Formula I-Id, and a pigment (e.g., oxides of silica, magnesium, calcium, aluminum, iron, titanium, zirconium, chromium, manganese, cobalt, cerium, nickel, zinc and composites and mixtures thereof).

In one embodiment, the cosmetic composition further comprises a catalyst preferably selected from among bismuth trifluoroacetate, bismuth triacetate, cerium chloride and mixtures thereof.

In another aspect of the invention, methods of reversibly adhering a benefit agent to keratinous substrates are provided comprising the step of applying to a keratinous surface a composition comprising a reaction product of any of the compounds for reversibly adhering a benefit agent to keratinous substrates described herein, including those of Formula I-Id, and a benefit agent having one or more reactive hydroxyl groups.

In a preferred embodiment, a method of reversibly adhering a benefit agent to keratinous substrates comprises the step of applying to a keratinous surface a composition comprising a reaction product of a compound having the structure of Formula Ic:

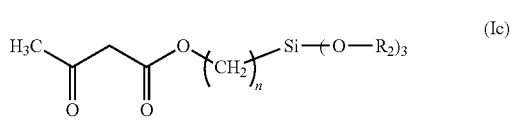

wherein $R_2$ is as identified above, but is typically independently selected at each occurrence from methyl and ethyl groups, and n is an integer from 3 to 5; and an inorganic oxide particle (e.g., silica or metal oxides where the metal is preferably selected from among magnesium, calcium, aluminum, iron, titanium, zirconium, chromium, manganese, cobalt, cerium, nickel, zinc and composites and mixtures thereof). Preferably, the inorganic oxide is selected from among titanium dioxide, zinc oxide, iron oxide or mixtures thereof. The method may further comprise the step of removing the benefit agent by contacting the keratinous substrate having the benefit agent adhered thereto with an amine containing solution, preferably the amine containing solution includes amino acids.

In a preferred aspect, the invention provides a reaction product of an inorganic oxide particulate have a median particle size of at least 5 nm and butanoic acid, 3-oxo, 3-(triethoxysilyl)propyl ester. The inorganic oxide particulate may be, without limitation, silica, alumina, iron oxide, titanium oxide, zinc oxide, or the like, and may have a median particle size ranging from about 10 nm up to about 100 microns or even larger, typically, from about 10 nm to about 100 nm, or about 100 nm to about 10 microns, or about 10 microns to about 20 microns, or about 20 microns to about 50 microns.

In yet another implementation, a method is provided for forming a durable deposit on a keratinous surface comprising depositing on said surface a surface-functionalized benefit agent comprising a first particulate agent surface-functionalized with a linker having reactive beta-diketo functional groups and a second particulate agent having amine groups reactive with said beta-diketo functional groups to thereby form a deposit comprising said first particulate agent covalently bound through said linker to said second particulate agent. The first particulate agent may be deposited as a first layer on said keratinous surface and the second particulate agent may deposited as a second layer over said first layer to bind the second layer to the first. Alternatively, the first particulate and the second particulate may be applied simultaneously or in admixture. The first and second particulates may, for example, each be a pigment, pearl, filler, or other powder having at least one optical characteristic (e.g., hue) different from the other.

In an additional implementation, a kit is provided comprising a first sealed package comprising a cosmetic composition for reversibly adhering a film to human skin, hair, or nails, comprising a benefit agent functionalized with a beta-diketo moiety that is reactive with amino-groups on the surface of said skin, hair or nails, and optionally a catalyst (e.g., a bismuth catalyst) and a second sealed package comprising an amine-containing compound (e.g., an amino acid), optionally in combination with a topically acceptable carrier, for removing the film from said human skin, hair, or nails.

These and other aspects of the present invention will become apparent to those skilled in the art after a reading of the following detailed description of the invention, including the illustrative embodiments and examples.

BRIEF DESCRIPTION OF THE DRAWINGS

FIG. 1 illustrates a reaction scheme for the synthesis of a beta dicarbonyl functionalized particle. In the embodiment illustrated, a beta dicarbonyl compound (1) is reacted with a particulate material having hydroxide groups (2) to form a reaction product which is a surface functionalized benefit agent (3).

DETAILED DESCRIPTION

In one aspect, the present invention provides novel compositions and methods comprising functionalized benefit agents for reversibly adhering a benefit agent to a keratinous substrate, newly found to form a durable cosmetic coating which may be removed when desired.

More specifically, the functionalized benefit agents of this invention are preferably obtained by reacting a benefit agent having one or more hydroxyl groups with a beta dicarbonyl compound including, without limitation, those of Formula I-Id. Preferably, the beta dicarbonyl compound is a beta diketo-ester. More preferably, the beta diketo-ester is covalently attached a benefit agent (e.g., to the surface of the pigment) through a siloxane linkage. Cosmetic compositions comprising the functionalized benefit agents have been newly found to covalently attach to proteins found in keratinous substrates and provide durable coatings that prevent the benefit agent from migrating or penetrating the skin. These functionalized benefit agents, or cosmetic compositions prepared therewith, have been newly determined to be reversibly attached to keratinous surfaces in accordance with the compositions and methods for treatment disclosed herein.

According to the present invention, yet without wishing to be bound by theory, it is believed that the beta dicarbonyl compounds including, without limitation, those of Formula I-Id, adhere to keratinous substrate proteins by reversible covalent bond formation (resulting in the formation of an imine/enamine moiety) via nucleophilic addition of a protein amino group (from the keratinous substrate) with a beta dicarbonyl carbon. The beta dicarbonyl compounds described herein, including those of Formula I-Id, further include a silicon alkoxide moiety that is capable of covalently bonding with benefit agents having a reactive functional group, e.g., a hydroxyl group (resulting in the elimination of an alcohol), and thereby producing a functionalized benefit agent. Upon application of a functionalized benefit agent to a keratinous substrate, the resulting covalent bond formation adheres the benefit agent to the skin and produces a long-wearing (until removal is desired), transfer resistant cosmetic or therapeutic agent having improved comfort to the integuments to which the benefit agent (e.g., cosmetic or therapeutic) is applied. For example, FIG. 1 illustrates a reaction of (1) a beta diketone functionalizing compound with (2) an inorganic particle having hydroxyl groups present on the surface thereof, thereby producing (3) a functionalized benefit agent that may be attached to the surface of a keratinous substrate.

In one aspect of the present invention, in its broadest view, encompasses any benefit agent, such as cosmetic or therapeutic materials, functionalized with the provided beta dicarbonyl compounds that reversibly react with keratinous substrate proteins, methods for the preparation thereof, cosmetic formulations prepared therewith, and their use in providing a durable topical application of benefit agents to keratinous substrates. Another aspect of the invention covers the novel beta dicarbonyl compounds including, without limitation, those of Formula I-Id.

As used herein, the term "keratinous substrate," used interchangeably with "keratinous surface" refers to keratin-containing layers disposed as the outermost protective covering of mammals which includes, but is not limited to, skin, lips, hair (including eyebrows and eyelashes), and nails (toenails, fingernails, cuticles, hooves, etc.) of mammalians, preferably humans.

The term "benefit agent" is used to describe cosmetic, dermatological, personal care, or pharmaceutical agents that provide aesthetic or therapeutic enhancement to a keratinous substrate, such as, human skin, hair or nails. Preferably, the benefit agent has one ore more functional groups capable of forming a covalent linkage to a trialkoxysilane. Typically, the functional group will be a hydroxyl functional group that forms a reaction product with a beta dicarbonyl compound as described herein, including, without limitation, those of Formula I-Id. In some embodiments, benefit agents do not include chelate forming metal including aluminum, magnesium, zirconium, titanium, iron, cobalt, nickel, chromium or manganese as described in U.S. Pat. No. 4,861,839. In one embodiment the benefit agent will be in a particulate form and have a particle size from 5 nm to 10 nm.

The phrase "non-transferable" or "transfer-resistant" refers to forming a deposit that does not become at least partially deposited onto the supports with which it comes into contact (e.g. glass, coffee cups, kiss proof, clothing, cigarettes).

The terms "a" and "an", as used herein and in the appended claims, mean "one or more" unless otherwise indicated herein.

Except where specific examples of actual measured values are presented, numerical values referred to herein should be considered to be qualified by the word "about."

In one aspect, the invention provides compounds for reversibly adhering a benefit agent to keratinous substrates, such as skin, lips, nails and/or hair, having the structure of Formula I and cosmetically suitable salts thereof:

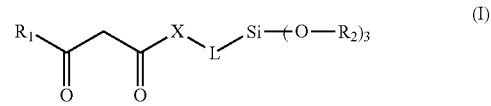

(I)

wherein $R_1$ is hydrogen or a $C_1$-$C_{20}$ hydrocarbon optionally substituted with 1-12 heteroatoms selected from oxygen, nitrogen, sulfur and halogen (e.g., Cl, F, Br, I etc.). Preferably, $R_1$ is a lower alkyl (e.g., $R_1$ is methyl, ethyl, propyl, butyl, pentyl or hexyl groups) and more preferred still, $R_1$ is methyl;

$R_2$ is independently selected at each occurrence from $C_1$-$C_7$ hydrocarbon optionally substituted with 1-4 heteroatoms selected from oxygen, nitrogen, sulfur and halogen. Preferably, $R_2$ is selected from among methyl, ethyl, propyl, butyl, pentyl, hexyl, phenyl or benzyl. More preferably, $R_2$ ethyl and/or methyl. Most preferably, $R_2$ is methyl.

X is a bond (i.e., X is absent), —O—, —$NR^N$—, —S—; wherein y and z are independently an integer from 1 to 10, (preferably from 1 to 5, more preferably 1-3);

L is a group of the form —$X_1$—$(CR^*_2)_n$—$X_2$—$(CR^*_2)_m$—$X_3$—; wherein $X_1$, $X_2$, and $X_3$ are independently at each occurrence a bond, —O—, —$NR^N$—, —S—, —$(OCH_2CH_2)_y$—, or —$(CH_2CH_2O)_z$—, wherein y and z are independently an integer from 1 to 10 (preferably from 1 to 3), and n and m are independently an integer from 0 to 10 (preferably from 1 to 3).

$R^N$ is independently at each occurrence hydrogen, methyl, ethyl, propyl, butyl, pentyl, hexyl, phenyl or benzyl and is most typically methyl or hydrogen.

$R^*$ is independently selected at each occurrence from H, $C_1$-$C_4$ alkyl (e.g., methyl, ethyl, propyl or butyl) or halogen (e.g., Cl, F, Br, I etc.) and is most typically methyl or hydrogen.

In another embodiment, the compound for reversibly adhering a benefit agent to a keratinous substrate has a structure according to Formula 1a and cosmetically suitable salts and derivatives thereof:

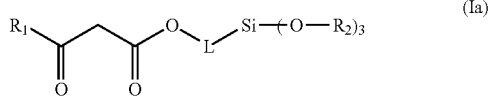

(Ia)

wherein $R_1$ is hydrogen or a $C_1$-$C_{20}$ hydrocarbon optionally substituted with 1-12 heteroatoms selected from oxygen, nitrogen, sulfur and halogen (e.g., Cl, F, Br, I etc.). Preferably, $R_1$ is a lower alkyl (e.g., $R_1$ is methyl, ethyl, propyl, butyl, pentyl or hexyl groups) and more preferred still, $R_1$ is methyl.

$R_2$ is independently selected at each occurrence from $C_1$-$C_7$ hydrocarbon optionally substituted with 1-4 heteroatoms selected from oxygen, nitrogen, sulfur and halogen. Preferably, $R_2$ is selected from among methyl, ethyl, propyl, butyl, pentyl, hexyl, phenyl or benzyl. More preferably, $R_2$ ethyl and/or methyl. Most preferably, $R_2$ is methyl.

L is a group of the form —$X_1$—$(CR^*_2)_n$—$X_2$—$(CR^*_2)_m$—$X_3$—; wherein $X_1$, $X_2$, and $X_3$ are independently at each occurrence a bond, —O—, —$NR^N$—, —S—, —$(OCH_2CH_2)_y$—, or —$(CH_2CH_2O)_z$—, wherein y and z are independently an integer from 1 to 10 (preferably from 1 to 3), and n and m are independently an integer from 0 to 10 (preferably from 1 to 3).

$R^N$ is independently at each occurrence hydrogen, methyl, ethyl, propyl, butyl, pentyl, hexyl, phenyl or benzyl and is most typically methyl or hydrogen.

$R^*$ is independently selected at each occurrence from H, $C_1$-$C_4$ alkyl (e.g., methyl, ethyl, propyl or butyl) or halogen (e.g., Cl, F, Br, I etc.) and is most typically methyl or hydrogen.

In a further embodiment, the compound for reversibly adhering a benefit agent to a keratinous substrate has a structure according to Formula 1b and cosmetically suitable salts and derivatives thereof:

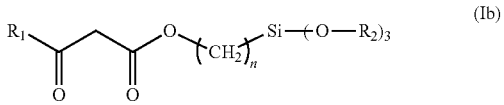

(Ib)

wherein $R_1$ is hydrogen or a $C_1$-$C_{20}$ hydrocarbon optionally substituted with 1-12 heteroatoms selected from oxygen, nitrogen, sulfur and halogen (e.g., Cl, F, Br, I etc.). Preferably, $R_1$ is a lower alkyl (e.g., $R_1$ is methyl, ethyl, propyl, butyl, pentyl or hexyl groups) and more preferred still, $R_1$ is methyl.

$R_2$ is independently selected at each occurrence from $C_1$-$C_7$ hydrocarbon optionally substituted with 1-4 heteroatoms selected from oxygen, nitrogen, sulfur and halogen (e.g., Cl, F, Br, I etc.). Preferably, $R_2$ is selected from among methyl, ethyl, propyl, butyl, pentyl, hexyl, phenyl or benzyl. More preferably, $R_2$ ethyl and/or methyl and most preferably, $R_2$ is methyl. In some, but not all embodiments, when $R_1$ is methyl, at least one (or two or three) of $R_2$ will not be methyl.

n is an integer from 0 to 10 (preferably from 1 to 3, most preferably, 3).

$R_2$ is independently selected at each occurrence from $C_1$-$C_7$ hydrocarbon optionally substituted with 1-4 heteroatoms selected from oxygen, nitrogen, sulfur and halogen (e.g., Cl, F, Br, I etc.). Preferably, $R_2$ is selected from among methyl, ethyl, propyl, butyl, pentyl, hexyl, phenyl or benzyl. More preferably, $R_2$ ethyl and/or methyl In one embodiment, the compounds for reversibly adhering a benefit agent to keratinous substrates have the structure of Formula Ic:

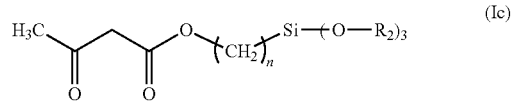

(Ic)

wherein $R_2$ is as identified above, but is typically independently selected at each occurrence from methyl and ethyl groups. In some, but not all embodiments, when $R_1$ is methyl, at least one (or two or three) of $R_2$ will not be methyl. n is an integer from 1 to 10 (preferably from 3-5, most preferably 3).

In one embodiment, the compounds for reversibly adhering a benefit agent to keratinous substrates have the structure of Id:

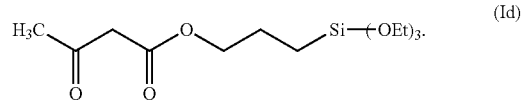

(Id)

In another aspect of the invention, methods of forming a functionalized benefit agent for reversibly adhering a benefit agent to a keratinous surface are provided. Typically the method will involve reacting a benefit agent having one or more hydroxyl groups with any of the compounds for reversibly adhering a benefit agent to keratinous substrates described herein, including those of Formula I-Id. Compound (Id) may reversibly bind to skin at a pH of about 3 to about 7, in one embodiment at physiological pH, including a pH of about 5 to about 7.

In some embodiments, the diketo carbonyl compound is present in a molar excess of the benefit agent. Typically, the proportion of diketo carbonyl compound to beta is from 1:1, 2:1, 10:1 up to 99:1 and even greater.

In some embodiments wherein the benefit agent includes particles, in particular, inorganic oxide particles, the amount of diketo carbonyl compound as a weight percent of the amount of benefit agent can range from 0.0001% or greater. Typically, 0.01% or greater. More typically, 0.1% or greater. The upper bounds of the weight percent of the diketo carbonyl compound can range up to 200% by weight, typically around 2% by weight of the amount of the benefit agent.

Another aspect of the invention is drawn to embodiments where the benefit agent is a pigment particle and provides pigments surface functionalized with a beta dicarbonyl compound including, without limitation, those of Formula I-Id. Preferably, the beta dicarbonyl compound is a beta diketo-ester. More preferably, the beta diketo-ester is covalently attached to the surface of the pigment particle through a siloxane linkage.

In another aspect of the invention, surface functionalized pigments for reversibly adhering to keratinous substrates are provided, wherein the surface functionalized pigment is a reaction product of any of the compounds for reversibly adhering a benefit agent to keratinous substrates described herein (including those of Formula I-Id) and an inorganic oxide particle (e.g., silica or metal oxides where the metal is preferably selected from among magnesium, calcium, aluminum, iron, titanium, zirconium, chromium, manganese, cobalt, cerium, nickel, zinc and composites and mixtures thereof).

Exemplary inorganic pigments include, but are not limited to, inorganic oxides and hydroxides such as magnesium oxide, magnesium hydroxide, calcium oxide, calcium hydroxides, aluminum oxide, aluminum hydroxide, iron oxides ($\alpha$-$Fe_2O_3$, y-$Fe_2O_3$, $Fe_3O_4$, FeO) and iron hydroxides including red iron oxide, yellow iron oxide and black iron oxide, titanium dioxide, titanium lower oxides, zirconium oxides, chromium oxides, chromium hydroxides, manganese oxides, manganese hydroxides, cobalt oxides, cobalt hydroxides, cerium oxides, cerium hydroxides, nickel oxides, nickel hydroxides, zinc oxides and zinc hydroxides and composite oxides and composite hydroxides such as iron titanate, cobalt titanate and cobalt aluminate and the like. Preferably, the inorganic oxide particles may be selected from silica, alumina, zinc oxide, and titanium dioxide particles, and mixtures thereof. Although silica, alumina, zinc oxide, and titanium dioxide particles are preferred, one of skill would understand that any particle which is capable of being functionalized by reaction with a siloxane may be used.

In one embodiment, the pigments are free of amine groups including primary amines or secondary amines.

In some embodiments, benefit agent is a particle. In one embodiment, the minimum particle size is 5 nm, 10 nm or even more typically, the minimum particle size is 50 nm. The particle size may range upwards from 1 micron, to 10 microns to 100 microns and above.

In one aspect, the invention provides cosmetic compositions comprising a surface functionalized benefit agent for reversibly adhering to keratinous substrates and a cosmetically acceptable vehicle, where the surface functionalized benefit agent is a reaction product of any of the beta dicarbonyl compounds described herein, including those of Formula I-Id, and a benefit agent (e.g., pigment particles, organic polymers, active ingredients).

In another aspect, the invention provides cosmetic compositions comprising a surface functionalized pigment for reversibly adhering to keratinous substrates and a cosmetically acceptable vehicle, where the surface functionalized pigment is a reaction product of any of the beta dicarbonyl compounds described herein, including those of Formula I-Id, and a pigment (e.g., oxides of silica, magnesium, calcium, aluminum, iron, titanium, zirconium, chromium, manganese, cobalt, cerium, nickel, zinc and composites and mixtures thereof).

In some embodiments, the functionalized benefit agent will typically be present in an amount from 0.1% to 95% by weight of the composition. More typically, the functionalized benefit agent will typically be present in an amount from 0.5% to 50% by weight of the composition, and even more typically, from 1 to 25% by weight of the composition.

Preferably, the cosmetic compositions provided herein do not include components bearing amine groups (e.g., primary or secondary amines) in such an amount as to inhibit the adhesion of the functionalized benefit agent to a keratinous substrate.

In a further embodiment, the cosmetics compositions provided herein do not include film forming polymers in such an amount as to produce a contiguous film on the surface of a keratinous substrate. In particular, film formers will be present in an amount less than that conventionally necessary for producing transfer resistant cosmetic formulations.

In a preferred embodiment, the cosmetic compositions provided herein further comprise catalysts which enhance the kinetics (i.e., increase the rate) of covalent bond formation between the protein binding domain and one or more protein amine functional groups from a keratinous substrate. Preferably, the catalyst enables a more saturated benefit agent effect and/or a reduced time period for the adhesion of the benefit agent to occur. Catalysts may be selected from among bismuth trifluoroacetate, bismuth triacetate and cerium chloride and the like. Other cosmetically acceptable molecules or compounds having such a catalytic effect may be also used in accordance with the present inventions, as understood by a person of ordinary skill in the art.

Particularly preferred embodiments of the present invention are drawn cosmetic compositions having functionalized benefit agents including, but not limited to, alpha-hydroxy acids, beta hydroxyl acids, ascorbic acid or Vitamin C and derivatives thereof (e.g., $C_1$-$C_8$ esters thereof); retinoids such as retinol (Vitamin A) and the esters thereof (e.g., $C_1$-$C_8$ esters, such as palmitate), retinoic acid and the derivatives thereof, hyaluronic acid, chemical sun screens useful in the cosmetic field including any UVA and UVB filter useful in the cosmetic field including mixtures thereof and blends with physical filters including, but not limited to metal oxide particles such as titanium oxides and/or zinc oxides. Preferred benefit agents also include pigments such as iron oxides, zirconium oxides, cerium oxides or mixtures thereof.

Additional preferred embodiments of the present invention are drawn to functionalized benefit agents formed by reacting any of the beta dicarbonyl compounds described herein with a benefit agent including botanicals (e.g., *Butea Frondosa* extract, *Asmunda japonica* extract, *Melicope hayesii* extract, *Derris scandens* Benth extract, *Tiliacora triandra* extract etc.); thiodipropionic acid (TDPA) and esters thereof; retinoids (e.g., all-trans retinoic acid, 9-cis retinoic acid, phytanic acid and others); hydroxy acids (including alpha-hydroxyacids and beta-hydroxyacids), salicylic acid and salicylates; exfoliating agents (e.g., glycolic acid, 3,6,9-trioxaundecanedioic acid, etc.), depigmenting agents (e.g., hydroquinone) estrogen synthetase stimulating compounds (e.g., caffeine and derivatives); compounds capable of inhibiting 5 alpha-reductase activity (e.g., linolenic acid, linoleic acid, finasteride, and mixtures thereof); antioxidants (e.g., thiodipropionic acid, vitamin E, etc.), barrier function enhancing agents (e.g., ceramides, glycerides, cholesterol and its esters, alpha-hydroxy and omega-hydroxy fatty acids and esters thereof, etc.); collagenase inhibitors; and elastase inhibitors; to name a few.

Preferred benefit agents that may be functionalized as described herein, in accordance with the present invention, may be therapeutic agents including, but not limited to, colorants (e.g., pigments, lakes or dyes), anti-acne agents, sunscreens, self-tanning ingredients, anti-inflammatory agents, antiseptic agents, insect repellants, anti-bacterials, anti-fungals, anti-virals, anti-yeast agents, age spot treatments, antioxidants, moisturizing agents, antiseptic agents, anti-oxidants, moisturizing agents, analgesics, antidandruff and antiseborrhetic agents, hyperkeratolytics, antipsoriatic agents, skin lightening agents, depigmenting agents, wound healing agents, burn treatments, tanning agents, hair treatment agents, hair growth products, wart removers, hormones, antipyretics, agents for lupus, multiform erythema, photo allergic and photo toxic reaction and atopic dermatitis or a body personal care composition, such as an antiperspirant or deodorant.

In some embodiments, the benefit agent may be modified or derivatized to react with a beta dicarbonyl compound disclosed herein including, without limitation, those of Formula I-Id. For example, benefit agents such as tuflon powders, polyolefin powders, silicon elastomer powders and poly(meth)acrylates which do not inherently posses a functional group for reacting with the beta dicarbonyl compounds disclosed herein, but these materials can be derivatized prior to functionalizing as described herein.

The invention also relates to cosmetic compositions comprising functionalized benefits agents, such as those aforementioned, for the therapeutic treatment of the skin.

In another aspect of the invention, methods of reversibly adhering a benefit agent to keratinous substrates are provided comprising the step of applying to a keratinous surface a composition comprising a reaction product of any of the compounds for reversibly adhering a benefit agent to keratinous substrates described herein, including those of Formula I-Id, and a benefit agent having one or more reactive hydroxyl groups.

In a preferred embodiment, a method of reversibly adhering a benefit agent to keratinous substrates comprises the step of applying to a keratinous surface a composition comprising a reaction product of a compound having the structure of Formula Ic:

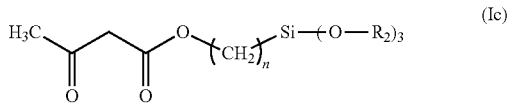

(Ic)

wherein $R_2$ is as identified above, but is typically independently selected at each occurrence from methyl and ethyl groups, and n is an integer from 3 to 5; and an inorganic oxide particle (e.g., silica or metal oxides where the metal is preferably selected from among magnesium, calcium, aluminum, iron, titanium, zirconium, chromium, manganese, cobalt, cerium, nickel, zinc and composites and mixtures thereof). Preferably, the inorganic oxide is selected from among titanium dioxide, zinc oxide, iron oxide or mixtures thereof. The method may further comprise the step of removing the benefit agent by contacting the keratinous substrate having the benefit agent adhered thereto with an amine-containing solution; preferably the amine containing solution includes amino acids.

Without being bound by theory, it is believed that topical application of the cosmetic composition of the present invention results in reversible covalent bond formation with proteins in the keratinous surface which serves to prevent migration or transfer of the functionalized pigment which is held at the surface of the keratinous substrate. The benefit agent may be removed by topical application of a solution including amines, such as amino acids (e.g., glycine, lysine, asparagine, glutamine, etc.).

The cosmetic composition of the present invention may be in the form of make-ups or color cosmetics such as foundation, foundation primer base, blush, lipstick, eyeshadow, eye liner, nail enamel, concealer, mascara, body make-up product, a sunscreen, or hair makeup product. The cosmetic compositions may be in the form of cosmetically acceptable vehicles, such as, but not limited to, liquid (e.g. suspension or solution), gel, emulsion, emulsified gel, mousse, cream, ointment, lotion, spray, wipe, paste, serum, milk, foam, balm, aerosol, liposomes, solid (e.g. pressed powders), cake, mask, anhydrous oil and wax composition. More specifically, the cosmetic may include an anti-sun product such as sunscreen or a skin coloring product such as a self-tanning product. The composition may also be a hair care product, especially for thickening, holding or shaping the hair or hairstyle.

Preferred embodiments of cosmetic compositions of the present invention are i) color cosmetics, including, but not limited to, foundation, lipstick, blush, etc.; ii) skin care products, including, but not limited to, anti-microbials, anti-acne, aesthetic modifiers, SPF products, sunless tanning products, long-lasting hydration products, anti-aging products that require the localized accumulation of active ingredients on the surface of the skin rather than having them penetrate into skin; and iii) haircare products with prolonged shine, conditioning, and/or coloring.

More preferably, the cosmetic composition of the present invention is especially suitable where long-lasting cosmetic effects are desired such as sunscreens, insect repellants, lipstick, lip gloss, mascara, foundation, leave on conditioners for damaged hair, semi-permanent makeup products such as tattoos, dots or patches that adhere to the skin (such as beauty marks or glitters) as well as skin care products such as masks, and overnight treatments.

In a preferred embodiment, a topical sunscreen composition comprising at least one functionalized benefit agent is provided wherein the functionalized benefit agent is a reaction product of a compound for reversibly adhering a benefit agent to keratinous substrates as described herein with one sunscreen active agent. Typically, the functionalized benefit agent is a reaction product with titanium dioxide and/or zinc oxide. The topical sunscreen of the present invention enhances the substantivity, waterproofness, sweat resistance and rub off resistance in a topical sunscreen composition.

Other suitable ingredients may be included as long as they do not interfere with the adhesion of the functionalized benefit agent of the present invention as understood by the skilled artisan. For example, the topical sunscreen of the present invention will comprise a cosmetically acceptable vehicle and may further comprise dibenzoylmethane, terephthalylidene dicamphor sulfonic acid, phenylbenzimidazole sulfonic acid, PABA, ethyl PABA, octyl dimethyl PABA, cinoxate, oxybenzone, dioxybenzone, octyl triazone, homosalate, rolamine salicylate, TEA salicylate, homomethyl salicylate, octyl salicylate, menthylanthranilate, octocrylene, octyl methoxycinnamate, padimate O, sulisobenzone, DEA methoxycinnamate, drometrizole trisiloxane, octyl methoxycinnamate, 4-methyl benzilidene camphor, hydroxy methylphenyl benzotriazole, methylene bis-benzotriazoyltetramethyblbutylphenol, bis-ethylhexyloxyphenol methoxyphenol triazine, and any derivatives thereof, and any combinations thereof.

In an additional preferred embodiment, a hair care composition comprising at least one functionalized benefit agent is provided wherein the functionalized benefit agent is a reaction product of a compound for reversibly adhering a benefit agent to keratinous substrates as described herein with at least one hair conditioning agent known in the art, e.g., silicone polyurethane polymers, film-forming esters, fluorosilicones, cationic conditioning polymers, and the like. The hair care product of the present invention provides durable color, long lasting shine, gloss and luster.

Other suitable hair care ingredients may be included as long as they do not interfere with the adhesion of the functionalized benefit agent of the present invention. For example, the hair care composition of the present invention will comprise a cosmetically acceptable vehicle and may further comprise volatile and non-volatile silicones, thickeners which may be nonionic, cationic, anionic or amphoteric.

In another embodiment of the invention, the hetero-bifunctional linkers of the invention (e.g., butanoic acid, 3-oxo, 3-(triethoxysilyl)propyl ester) may, in addition to, or instead of linking a benefit agent (e.g., a pigment) directly to the keratinous surface, may link the benefit agent to a second benefit agent, which is typically different than the first benefit agent. In this embodiment, a second benefit agent is provided which has reactive amino groups on the surface which are reactive with the diketo moieties of the hetero-bifunctional linkers of the invention. As an illustration of this embodiment, a hetero-bifunctional linker, such as butanoic acid, 3-oxo, 3-(triethoxysilyl)propyl ester, may be first reacted with a first particulate benefit agent (e.g., a first pigment having a first optical attribute) by condensation of the trialkoxysilyl functionality with free surface hydroxyl groups on the pigment to form a first surface functionalized benefit agent. The resultant surface functionalized pigment may be applied as a first layer to a keratinous surface to reversibly adhere thereto, and a second layer may be deposited over the first layer, the second layer comprising a second particulate benefit agent (e.g., a second pigment having a second optical attribute different from the first optical attribute) which has amino groups capable of reacting with the diketo moiety of the first surface functionalized particulate to form a durable, reversibly bound second layer over the first. The optical attributes may include, without limitation, hue, chroma, pearlescense or optical interference, UV absorption, or any other such attribute. Additional layers may be deposited over the second layer, including for example, a further layer of the first surface functionalized particulate to form a third layer reversibly adhered to the second layer. Alternatively, the first functionalized benefit agent may be admixed with the second benefit agent either prior to application to a keratinous surface or after deposit onto the keratinous surface to form a complex network having the first and second benefit agents covalently bound to one another through the linker. The second benefit agent may be any specifies that has a benefit to a keratinous surface, that is biologically compatible, and which possesses one or more free amino groups (preferably primary amino groups) that can react with the diketo (e.g., beta-diketo) functional group of the hetero-bifunctional linker. Examples include synthetic polymers such as polylysine, natural polymers such as chitosan and other mucopolysaccharides, pigments (e.g., metal oxides) that are surface functionalized with amine-bearing species such as, without limitation, amodimethicones and alkylamines, to name a few. A lip product may be provided according to this embodiment, where bother the first and second particulates are delivered from the same stick. The stick (e.g., a solid or semi-solid wax, polymer, or gel-based lipstick) may be of the dual core type which contains an inner core of the first composition and an annular ring around the inner core containing the second pigment. In the way the reaction is prevented or retarded until the composition is admixed on the lips. A catalyst (e.g. bismuth) may be included in either part.

The compositions of the invention may optionally comprise other active and inactive ingredients typically associated with cosmetic and personal care products as long as they do not interfere with the adhesion of the functionalized benefit agent of the present invention, including, but not limited to, excipients, fillers, emulsifying agents, antioxidants, surfactants, film formers, chelating agents, gelling agents, thickeners, emollients, humectants, moisturizers, vitamins, minerals, viscosity and/or rheology modifiers, sunscreens, keratolytics, depigmenting agents, retinoids, hormonal compounds, alpha-hydroxy acids, alpha-keto acids, anti-mycobacterial agents, antifungal agents, antimicrobials, antivirals, analgesics, lipidic compounds, antiallergenic agents, H1 or H2 antihistamines, anti-inflammatory agents, anti-irritants, antineoplastics, immune system boosting agents, immune system suppressing agents, anti-acne agents, anesthetics, antiseptics, insect repellents, skin cooling compounds, skin protectants, skin penetration enhancers, exfollients, lubricants, fragrances, colorants, staining agents, depigmenting agents, hypopigmenting agents, preservatives, stabilizers, pharmaceutical agents, photostabilizing agents, and mixtures thereof. In addition to the foregoing, the compositions of the invention may contain any other compound for the treatment of skin disorders.

Other Ingredients Optionally Included in Cosmetic Compositions

1. Shine Agents

The cosmetic compositions of the invention may optionally include one or more agents that provide or enhance shine. Shine enhancing agents will typically have a refractive index greater than about 1.4, preferably greater than about 1.5 when measured as a film at 25° C. Suitable shine enhancing agents include without limitation, polyols, fatty esters, silicone oils, phenylpropyldimethylsiloxysilicate, polybutene, polyisobutene, hydrogenated polyisobutene, hydrogenated polycyclopentadiene, propyl phenyl silsesquioxane resins; lauryl methicone copolyol, perfluorononyl dimethicone, dimethicone/trisiloxane, methyl trimethicone, and combinations thereof. In one embodiment, the composition will comprise a shine-enhancing agent in an amount from about 0.1% to about 10% by weight, more preferably from about 1% to about 5% by weight, based on the total weight of the composition.

2. Waxes

The cosmetic compositions of present invention may optionally include one or more waxes. The one or more waxes can be natural (e.g., vegetable, animal, or mineral) waxes or synthetic waxes (e.g., polyolefine, Fisher Tropsch, etc.). A preferred wax is microcrystalline waxes, which will preferably be composed of C8 to C50 hydrocarbons and will have a melting point preferably greater than about 60° C. Other waxes that may be mentioned include, without glyceryl tribehenate, candelilla, carnauba, ozokerite, paraffin, polyethylene, beeswax, ceresin, hydrogenated castor oil, japan wax, and mixtures thereof, in one embodiment, the amount of wax is less than about 2 wt % of the total weight of the composition. In another embodiment, the amount of wax ranges from about 0.1% to less than about 2% by weight based on the total weight of the composition. However, more wax can be used if clarity is not a concern. For example, a lip stick may comprise wax from about 5% to about 25% by weight based on the weight of the composition.

3. Pigments and Fillers

The cosmetic compositions may optionally further comprises various other pigments, pearlescents, dyes, lakes, and fillers, as is customary in a given product. These include, without limitation, metal oxide pigment such as iron oxides and titanium dioxide, silica, alumina, nylon powder, Teflon powder, PMMA, silicone elastomers, and the like. For other pigments, lakes and dyes used in cosmetic industry, refer to the Cosmetic Ingredient Dictionary (INCI) and Handbook, 12th Edition (2008), published by the Cosmetic, Toiletry, and Fragrance Association (CTFA), the disclosure of which is hereby incorporated by reference. Such additional pigments, tillers and the like will typically comprise from about 0.1% to about 20% by weight of the composition, more typically from about 0.8% to about 10% by weight of the composition.

4. Film Formers

The cosmetic compositions may optionally further comprise film formers which act synergistically with the functionalized benefit agents of the present invention to prevent or inhibit transfer of the benefit agent, other water-soluble, water-dispersible, or water-insoluble film formers, including film forming polymers, may be employed. The term filmforming polymer may be understood to indicate a polymer which is capable, by itself or in the presence of at least one auxiliary film-forming agent, of forming a continuous film which adheres to a surface and functions as a binder for the particulate material.

Polymeric film formers include, without limitation, acrylic polymers or co-polymers, acrylates, polyolefins, polyvinyls, polacrylates, polyurethanes, silicones, polyamides, polyethers, polyesters, fluoropolymers, polyethers, polyacetates, polycarbonates, polyamides, polyimides, rubbers, epoxies, formaldehyde resins, organosiloxanes, dimethicones, methicones, cellulosics, polysaccharides, polyquaterniums, and the like. Suitable film formers include those listed in the Cosmetic Ingredient Dictionary (INCI and Handbook, 12.sup.th Edition (2008), the disclosure of which is hereby incorporated by reference.

5. Cosmetically Acceptable Vehicles

The compositions will typically comprise a cosmetically acceptable vehicle. By "cosmetically acceptable" is meant that the vehicle is safe for contact with human skin. It is contemplated that any cosmetically acceptable vehicle known in the art will be useful. The vehicle may comprise water, hydrophobic, and/or hydrophilic solvents.

Suitable hydrophilic solvents include but are not limited to, water, isopropyl alcohol, ethyl alcohol, glycerin, butylene glycol, propylene glycol, pentylene glycol, caprylyl glycol, polyglycerol diisostearate, dimethylsiloxane/glycol copolymer, isopropyl myristate, triisostearyl citrate, or any combinations thereof. Suitable hydrophobic vehicles include volatile or non-volatile hydrocarbon oils, silicones, fatty ester oils, and the like.

The compositions may comprise at least one high evaporation rate solvent in combination with at least one medium evaporation rate solvent and/or at least one slow evaporation rate solvent. As used herein, a high evaporation rate solvent may be characterized as a solvent that exhibits about 20% to about 40% weight loss at 35° C. over 60 minutes and/or about 40% to about 50% weight loss at 35° C. over 120 minutes. A medium evaporation rate solvent may be characterized as a solvent that exhibits about 10% to about 15% weight loss at 35° C. over 60 minutes and/or about 20% to about 30% weight loss at 35° C. over 120 minutes. A slow evaporation rate solvent may be characterized as a solvent that exhibits less than about 10% weight loss at 35° C. over 60 minutes and/or about 5% to about 15% weight loss at 35° C. over 120 minutes. Non-limiting example of high evaporation rate solvents include hexamethyl disiloxane and/or a silicone fluid having a viscosity of less than 1 cSt at 25° C., including, for example, those silicone fluids having a viscosity of 0.65 cSt. A non-limiting example of a medium evaporation rate solvent include mixed dimethicones, e.g., a dimethicone/trisiloxane blend. Non-limiting examples of slow evaporation rate solvents include cyclopentasiloxane, methyl trimethicone, and isododecane.

The compositions of the invention may, in some embodiments, be provided as anhydrous formulations. By "anhydrous" is mean that the weight percentage of water in the composition is less than about 1% by weight. Preferably, the anhydrous compositions are substantially free of water by which is meant that water is not deliberately added to the compositions and the level of water is no more than would be expected based on the absorption of water from the air.

The vehicle may comprise from about 5% to about 99% by weight of the composition, typically from about 30% and about 90% by weight, and more typically from about 50% and about 70% by weight of the composition.

5. Emulsions

The compositions according to the invention may be formulated as water-in-oil (W/O) emulsions, oil-in-water (O/W) emulsions, water-in-silicone, silicone-in-water emulsions, and the like. These emulsions comprise a continuous phase and a discontinuous phase. The continuous phase may be aqueous, oil-based, or silicone-based and the discontinuous phase may likewise be aqueous, oil-based, or silicone-based, depending on the nature of the continuous phase. Combined oil and silicone phases are also possible.

The oil phase may comprise any of the hydrophobic oils discussed herein, including, without limitation, vegetable oils; fatty acid esters; fatty alcohols; isoparaffins such as isododecane; silicone oils such as dimethicones, cyclic silicones, and polysiloxanes; hydrocarbon oils such as mineral oil, petrolatum, isoeicosane and polyisobutene; natural or synthetic waxes; and the like.

The emulsions will typically comprise an amount of emulsifier sufficient to stabilize the emulsion. The amount of emulsifier will typically be from about 0.001 wt % to about 20 wt %, but preferably will range from about 0.01 to about 10 wt %, and most preferably about 0.1 wt % to about 5 wt %, based upon the total weight of the composition.

6. Emollients

The cosmetic compositions may optionally comprise one or more emollients in an amount from about 0.1% up to about 20% by weight, based on the total weight of the composition. More typically, emollients will be present in an amount from about 2 wt % to about 15 wt %, preferably, about 5 wt %. Emollients useful in the present invention include any known to the art, including, but not limited to, oils and esters, such as lanolin and petrolatum. Other emollients include jojoba oil, lanolin oil, coconut oil, palm kernel glycerides, grape seed oil, evening primrose oil, sesame oil, castor oil, meadowfoam seed oil, emu oil, dimethicone copolyol meadowfoamate, wheat germ oil, macadamia nut oil, avocado oil, and mixtures thereof.

7. Thickeners

The composition may comprise a thickener, such as vegetable gums, carboxymethyl cellulose, silica, acrylic acid polymers, clays, such as hectorites, bentonites, hydrated magnesium and aluminium silicates, or calcium silicates, or the like. When present, thickeners will comprise from about 0.1% to about 15% by weight of the composition, more typically from about 1% to about 5% by weight of the composition.

8. Other Ingredients

The composition may comprise one or more preservatives such as methyl, ethyl, or propyl paraben, and so on, in amounts ranging from about 0.0001 wt %-5 wt % by weight of the total composition. The compositions may have other ingredients such as one or more anesthetics, anti-allergenics, antifungals, anti-inflammatories, antimicrobials, antiseptics, chelating agents, emollients, emulsifiers, fragrances, humectants, lubricants, masking agents, medicaments, moisturizers, pH adjusters, preservatives, protectants, soothing agents, stabilizers, sunscreens, surfactants, thickeners, viscosifiers, vitamins, or any combinations thereof.

In addition, a cosmetic composition according to the present invention may comprise other ingredients and additives known in the art, depending on the purpose for which the cosmetic is intended. For example, a composition described herein may optionally include one or more functional agents, fillers and fragrances.

The compositions according to the invention may be useful in a variety of cosmetic and personal care products, including without limitation, lipsticks, and lipcolors, lip gloss, mascaras, transfer-resistant foundations, eyeliner, eyeshadow, water-proof sunscreens and insect repellents, skin care products, hair care products, antiperspirants and deodorants, and other cosmetic products where transfer resistant films are desired.

In another embodiment, the invention is formulated in a conventional lipstick or lipcolor product and may include, without limitation, any of the components disclosed in U.S. Pat. No. 6,509,009, U.S. Pat. No. 6,428,797, U.S. Pat. No. 6,261,576, U.S. Pat. No. 5,747,017, U.S. Pat. No. 5,318,775, and U.S. Pat. No. 4,935,228, the disclosures of which are hereby incorporated by reference.

EXAMPLES

The following example describes specific aspects of the invention to illustrate the invention and provide a description of the present methods for those of skill in the art. The example should not be construed as limiting the invention, as the examples merely provide specific methodology useful in the understanding and practice of the invention and its various aspects.

Example 1

Preparation of Butanoic acid, 3-oxo, 3-(triethoxysilyl)propyl ester

Butanoic acid, 3-oxo, 3-(triethoxysilyl)propyl ester is prepared by reacting an slight molar excess trimethoxysilane with 3-oxo-butyric acid allyl ester according to the reaction scheme below.

Scheme 1

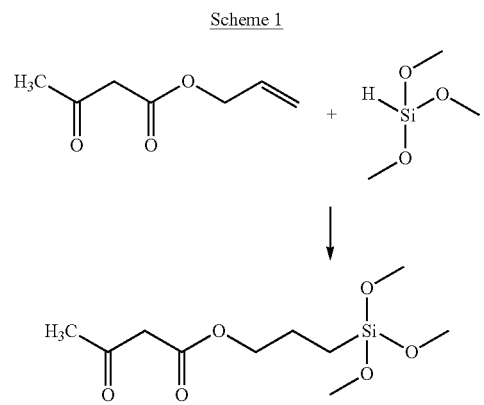

Example 2

Preparation of Diketoalkyl Siloxanes

Hydroxypropyl triethoxysilane (2b) was prepared by reacting tiethoxysilane (2a) with allyl alcohol in the presence of dihydrogen hexachloro palatinate catalyst according to reaction scheme 2.

Scheme 2

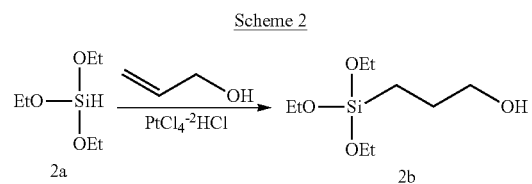

Compound 2b can be coupled to a diketo compound through a variety of couple reactions. The synthesis of butanoic acid, 3-oxo, 3-(triethoxysilyl)propyl ester (2) may proceed through the reaction of 2b with diketene as shown below.

Scheme 3

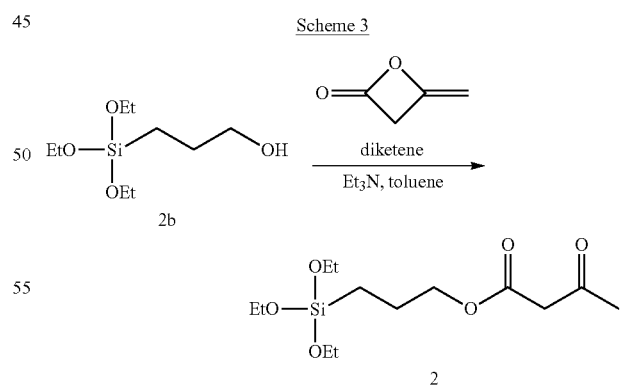

A more generalized synthetic route begins with a ester or diester which can be couple to a hydroxyalkyl tiralkoxysilane such as 2b through an intermediate acid halide or through the use of a coupling reagent such as dicyclohexyl carbodiimide (DCC). The in situ generation of an acid chloride can proceed from diethyl malonate (3a) via a base hydrolysis to the monoester (3b) and to the chloride by treatment with thionyl chloride (SOCl$_2$), phosphorus trichloride (PCl$_3$), or phosphorus pentachloride (PCl$_5$), for example. An illustrative scheme is shown below:

Scheme 4

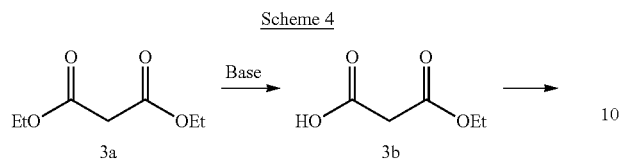

Acyl chloride 3c readily reacts with compound 2b to afford the final compound 3, as shown below.

Scheme 5

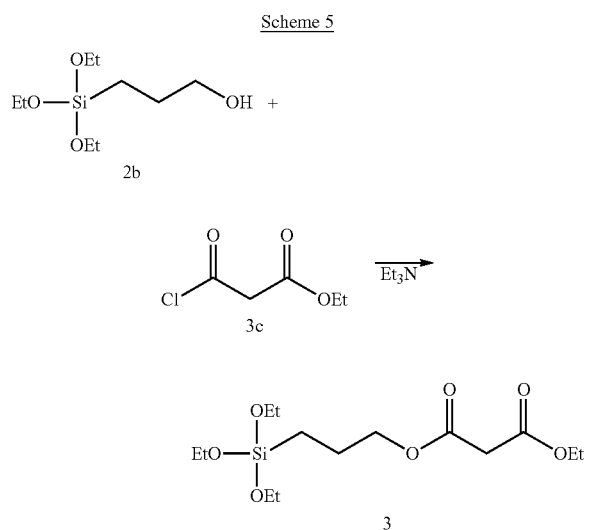

It will be apparent that the foregoing synthetic route may be readily generalized to a variety of starting materials of the form EtO—(C=O)—CH$_2$—(C=O)—R, where R is alkyl, alkoxy, haloalkyl, aryl, alkyl-aryl (e.g., benzyl), and the like.

In a related synthetic route from compound 2b, the coupling is carried out with a coupling agent such as DCC, as shown below.

Scheme 6

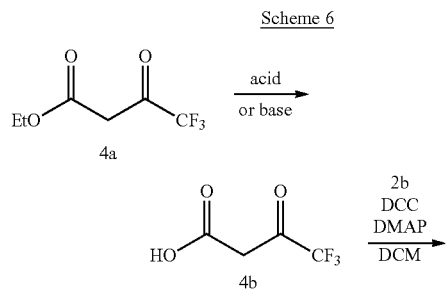

-continued

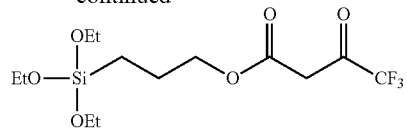

Example 3

Preparation of Functionalized Silica Oxide

Functionalized silica oxide was prepared by reacting the compound having the structure of formula Ic, i.e., butanoic acid, 3-oxo(3-triethoxysilyl)propyl ester, with silica oxide powder and then isolating and washing the silica oxide particles once the reaction is complete. 2,4-dinitrophenylhydrazine (DPH) stain is prepared according to known methods. Addition of the DPH stain to a sample of the treated silica oxide particles indicates the presence of carbonyl groups confirming that the silica oxide has been functionalized.

Example 3

Evaluation of Adhesion with Skin

Vitro-Skin® and ninhydrin stain were used to evaluate the efficacy of adhesion of the compounds for reversibly adhering a benefit agent to keratinous substrates. Vitro-Skin® is an advanced testing substrate that effectively mimics the surface properties of human skin. Ninhydrin is prepared according to standard methods and causes a stain to develop specific for amino acids, amino sugars and primary, secondary, and tertiary amines.

Under aqueous conditions, Vitro-Skin® has amino groups which react with the Ninhydrin stain. Upon treatment of the Vitro-Skin® with the compound prepared according to Example 1, i.e., butanoic acid, 3-oxo, 3-(triethoxysilyl)propyl ester, the amines are reacted and significant ninhydrin stain does not develop. Use of Bi(OAc)$_3$ catalyst provides a greater saturation of the Vitro-Skin® surface and essentially no stain develops. Reversibility of the adhesion is confirmed by treating the pre-reacted vitro-skin with a solution containing amino acids and staining with ninhydrin. A significant stain develops in all three cases.

Under anhydrous conditions (i.e., using diisostearyl fumarate), Vitro-Skin® has amino groups which react with the Ninhydrin stain. Upon treatment of the Vitro-Skin® the compound prepared according to Example 1, i.e., butanoic acid, 3-oxo, 3-(triethoxysilyl)propyl ester, the amines are reacted and only a small degree of ninhydrin stain develops. Use of Bi(OAc)$_3$ catalyst provides a greater saturation of the Vitro-Skin® surface and essentially no stain develops. Reversibility of the adhesion under anhydrous conditions is confirmed by treating the pre-reacted vitro-skin with a solution containing amino acids and staining with ninhydrin. A significant stain develops in all three cases.

Sample Embodiments

1. A method of forming a functionalized benefit agent for reversibly adhering a benefit agent to a keratinous surface comprising reacting a benefit agent having one or more hydroxyl groups with a compound having the structure of Formula (I) and cosmetically suitable salts thereof:

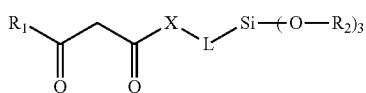

(I)

wherein $R_1$ is hydrogen or a $C_1$-$C_{20}$ hydrocarbon optionally substituted with 1-12 heteroatoms selected from oxygen, nitrogen, sulfur and halogen;

$R_2$ is independently selected at each occurrence from methyl, ethyl, propyl, butyl, pentyl, hexyl, phenyl or benzyl;

X is a bond, —O—, —$NR^N$—, or —S—; and

L is a group of the form —$X_1$—$(CR*_2)_n$—$X_2$—$(CR*_2)_m$—$X_3$—; wherein $X_1$, $X_2$, and $X_3$ are independently at each occurrence a bond, —O—, —$NR^N$—, —S—, —$(OCH_2CH_2)_y$—, or —$(CH_2CH_2O)_z$—, wherein y and z are independently an integer from 1 to 10, and "n" and "m" are independently an integer from 0 to 10;

$R^N$ is independently at each occurrence hydrogen, methyl, ethyl, propyl, butyl, pentyl, hexyl, phenyl or benzyl; and R* is independently selected at each occurrence from $C_1$-$C_4$ alkyl, H, or halogen;

wherein said benefit agent is in particulate form having a median particle size greater than about 5 nm.

2. A method of forming a benefit agent according to claim 1, wherein X is —O—.

3. A method of forming a benefit agent according to claim 2, wherein L is —$(CH_2)_n$—, where n is an integer from 1 to 10.

4. A method of forming a benefit agent according to claim 3, wherein n is an integer from 3 to 5.

5. A method of forming a benefit agent according to any one of claims 1-4, wherein $R_1$ is selected from the group consisting of methyl, ethyl, propyl, butyl, pentyl and hexyl groups.

6. A method of forming a benefit agent according to claim 5, wherein $R_1$ is a methyl group.

7. A method of forming a benefit agent according to any one of claims 1-4, wherein $R_2$ is independently selected at each occurrence from the group consisting of methyl, ethyl, propyl, butyl, pentyl and hexyl groups.

8. A method of forming a benefit agent according to claim 7, wherein $R_2$ is a methyl group.

9. A method of forming a benefit agent according to claim 1, having the structure of Formula (Ic):

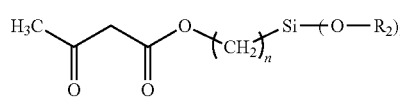

(Ic)

wherein $R_2$ is independently selected at each occurrence from methyl and ethyl groups, and n is an integer from 1 to 10.

10. A method of forming a benefit agent according to claim 1, having the following Formula (Id):

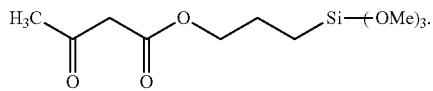

(Id)

11. A method of forming a benefit agent according to claim 1, having the following Formula (Ie):

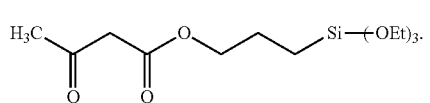

(Ie)

12. The method according to claim 1, wherein the benefit agent is an inorganic oxide particle.

13. The method according to claim 12, wherein the inorganic oxide is silica.

14. The method according to claim 12, wherein the inorganic oxide is a metal oxide.

15. The method according to claim 14, wherein the metal is selected from the group consisting of magnesium, calcium, aluminum, iron, titanium, zirconium, chromium, manganese, cobalt, cerium, nickel, zinc, and composites and mixtures thereof.

16. The method according to claim 15, wherein the metal oxide is titanium dioxide, zinc oxide, iron oxide or mixtures thereof.

17. The method according to claim 1, wherein the benefit agent is an organic polymer.

18. The method according to claim 17, wherein the organic polymer is biopolymer.

19. The method according to claim 18, wherein the biopolymer is hyaluronic acid, chitin, collagen, elastin, keratin, cellulose.

20. The method according to claim 19, wherein the benefit agent is an organic molecule having a molecular mass less than 1000 Da.

21. The reaction product of the method according to any one of claims 1-20.

22. A pigment surface functionalized with a flexible linker having a reactive beta dicarbonyl functional group, the pigment having a median particle size of at least about 5 nm.

23. The pigment of claim 22, wherein said median particle size is between 10 nm and 100 microns.

24. The pigment according to claim 23, wherein the flexible linker is covalently attached to the surface of the pigment through a siloxane linkage.

25. The pigment according to claim 22, wherein the pigment is an inorganic oxide particle.

26. The pigment according to claim 25, wherein the inorganic oxide is silica or a metal oxide wherein the metal is selected from the group consisting of magnesium, calcium, aluminum, iron, titanium, zirconium, chromium, manganese, cobalt, cerium, nickel, zinc, and composites and mixtures thereof.

27. A surface functionalized pigment for reversibly adhering a benefit agent to keratinous substrates, wherein the surface functionalized pigment is a reaction product of i) a compound according to any one of claims 1-20; and ii) an inorganic oxide particle having a median particle size greater than 5 nm, wherein the inorganic oxide is silica or a metal oxide where the metal is selected from the group consisting of magnesium, calcium, aluminum, iron, titanium, zirconium, chromium, manganese, cobalt, cerium, nickel, zinc and composites and mixtures thereof.

28. A surface functionalized pigment for reversibly adhering a benefit agent to keratinous substrates, wherein the surface functionalized pigment is a reaction product of
i) a compound having the structure of Formula Ic:
(Ic)

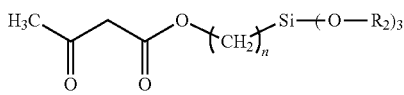

wherein $R_2$ is independently selected at each occurrence from methyl and ethyl groups, and n is an integer from 3 to 5; and
ii) an inorganic oxide having a median particle size great than 5 nm, wherein the inorganic oxide is silica or a metal oxide where the metal is selected from the group consisting of magnesium, calcium, aluminum, iron, titanium, zirconium, chromium, manganese, cobalt, cerium, nickel, zinc and composites and mixtures thereof.

29. The surface functionalized pigment according to claim 28, wherein the inorganic oxide is selected from the group consisting of titanium dioxide, zinc oxide, iron oxide and mixtures thereof.

30. A cosmetic composition comprising a surface functionalized pigment for reversibly adhering a benefit agent to keratinous substrates and a cosmetically acceptable vehicle, wherein the surface functionalized pigment is a reaction product of
i) a compound according to any one of claims 1-20; and
ii) a pigment selected from the group consisting of oxides of silica, magnesium, calcium, aluminum, iron, titanium, zirconium, chromium, manganese, cobalt, cerium, nickel, zinc and composites and mixtures thereof.

31. A cosmetic composition according to claim 30, wherein the composition further includes film forming polymers.

32. A cosmetic composition according to claim 30, wherein the composition is free of film forming polymers.

33. A cosmetic composition comprising a surface functionalized pigment for reversibly adhering a benefit agent to keratinous substrates and a cosmetically acceptable vehicle, wherein the surface functionalized pigment is a reaction product of
i) a compound having the structure of Formula I(c):
(Ic)

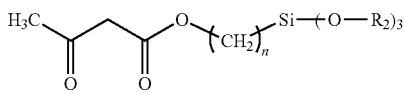

wherein $R_2$ is independently selected at each occurrence from methyl and ethyl groups, and n is an integer from 3 to 5; and
ii) a pigment having a median particle size of at least 10 nm, the pigment selected from the group consisting of oxides and hydroxides of silica, magnesium, calcium, aluminum, iron, titanium, zirconium, chromium, manganese, cobalt, cerium, nickel, zinc and composites and mixtures thereof.

34. A cosmetic composition according to claim 33, wherein the composition further includes one or more film forming polymers.

35. A cosmetic composition according to claim 33, wherein the composition is free of film forming polymers.

36. The cosmetic composition according to claim 33, further comprising a catalyst selected from the group consisting of bismuth trifluoroacetate, bismuth triacetate, cerium chloride and mixtures thereof.

37. A method for forming a durable deposit on human skin, nails, or hair, comprising applying thereto a functionalized pigment produced by the reaction of an inorganic oxide particulate have a median particle size of at least 5 nm with butanoic acid, 3-oxo, 3-(triethoxysilyl)propyl ester.

38. The method of claim 37, further comprising applying to the skin, nails, or hair, either prior to, concurrent with, or after the step of applying said functionalized pigment, a catalyst selected from the group consisting of bismuth trifluoroacetate, bismuth triacetate, cerium chloride and mixtures thereof.

39. The method of claim 37, further comprising the step of removing the benefit agent by contacting the surface of said keratinous substrate with an amine-containing solution.

40. The method of claim 52, wherein the amine containing solution comprises water and an amino acid.

41. A method for forming a durable deposit on a keratinous surface comprising depositing on said surface a surface-functionalized benefit agent comprising a first particulate agent surface-functionalized with a linker having reactive beta-diketo functional groups and a second particulate agent having amine groups reactive with said beta-diketo functional groups to thereby form a deposit comprising said first particulate agent covalently bound through said linker to said second particulate agent.

42. The method of claim 41, wherein said first particulate agent is deposited as a first layer on said keratinous surface and said second particulate agent is deposited as a second layer over said first layer.

43. The reaction product of an inorganic oxide particulate have a median particle size of at least 5 nm and butanoic acid, 3-oxo, 3-(triethoxysilyl)propyl ester.

44. A kit comprising:
(a) A first sealed package comprising a cosmetic composition for reversibly adhering a film to human skin, hair, or nails, comprising a benefit agent functionalized with a beta-diketo moiety that is reactive with amino-groups on the surface of said skin, hair or nails, and optionally a catalyst;
(b) A second sealed package comprising an amino acid, optionally in combination with a topically acceptable carrier, for removing the film from said human skin, hair, or nails.

The invention claimed is:
1. A method of forming a functionalized benefit agent for reversibly adhering a benefit agent to a keratinous surface comprising reacting a benefit agent having one or more hydroxyl groups with a compound having the structure of Formula (I) or cosmetically suitable salts thereof:

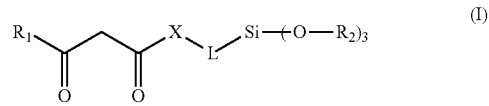

wherein $R_1$ is hydrogen or a $C_1$-$C_{20}$ hydrocarbon optionally substituted with 1-12 heteroatoms selected from oxygen, nitrogen, sulfur and halogen;
$R_2$ is independently selected at each occurrence from methyl, ethyl, propyl, butyl, pentyl, hexyl, phenyl or benzyl;
X is a bond, —O—, —NR$^N$—, or —S—; and L is a group of the form —$X_1$—$(CR^*_2)_n$—$X_2$—$(CR^*_2)_m$—$X_3$—; wherein $X_1$, $X_2$, and $X_3$ are independently at each occurrence a bond, —O—, —$NR^N$—, —S—, —$(OCH_2CH_2)_y$—, or —$(CH_2CH_2O)_z$—, wherein y and z are independently an integer from 1 to 10, and n and m are independently an integer from 0 to 10;

$R^N$ is independently at each occurrence hydrogen, methyl, ethyl, propyl, butyl, pentyl, hexyl, phenyl or benzyl; and $R^*$ is independently selected at each occurrence from $C_1$-$C_4$ alkyl, hydrogen, or halogen;

wherein said benefit agent is in particulate form having a median particle size greater than about 5 nm;

thereby producing a functionalized benefit agent which, upon application, reversibly adheres to a keratinous surface.

2. The method according to claim 1, wherein X is —O—.

3. The method according to claim 2, wherein L is —$(CH_2)_n$—, where n is an integer from 1 to 10.

4. The method according to claim 3, wherein n is an integer from 3 to 5.

5. The method according to claim 1, wherein $R_1$ is selected from the group consisting of methyl, ethyl, propyl, butyl, pentyl and hexyl groups.

6. The method according to claim 5, wherein $R_1$ is a methyl group.

7. The method according to claim 1, wherein $R_2$ is independently selected at each occurrence from the group consisting of methyl, ethyl, propyl, butyl, pentyl and hexyl groups.

8. The method according to claim 7, wherein $R_2$ is a methyl group.

9. The method according to claim 1, wherein the compound has the structure of Formula (Ic):

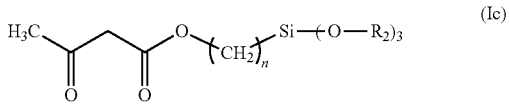

(Ic)

wherein $R_2$ is independently selected at each occurrence from methyl and ethyl groups, and n is an integer from 1 to 10.

10. The method according to claim 1, wherein the compound has the structure of Formula (Id):

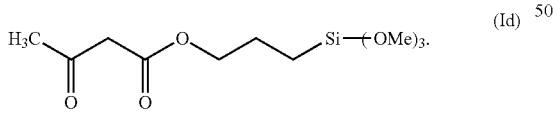

(Id)

11. The method according to claim 1, wherein the compound has the structure of Formula (Ie):

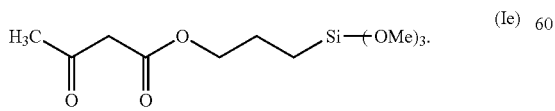

(Ie)

12. The method according to claim 1, wherein the benefit agent is an inorganic oxide particle.

13. The method according to claim 12, wherein the inorganic oxide is silica.

14. The method according to claim 12, wherein the inorganic oxide is a metal oxide.

15. The method according to claim 14, wherein the metal is selected from the group consisting of magnesium, calcium, aluminum, iron, titanium, zirconium, chromium, manganese, cobalt, cerium, nickel, zinc, and composites and mixtures thereof.

16. The method according to claim 15, wherein the metal oxide is titanium dioxide, zinc oxide, iron oxide or mixtures thereof.

17. The method according to claim 1, wherein the benefit agent is an organic polymer.

18. The method according to claim 17, wherein the organic polymer is biopolymer.

19. A method of reversibly adhering a benefit agent to a keratinous surface, comprising:

(1) providing a functionalized benefit agent by reacting a benefit agent having one or more hydroxyl groups with a compound having the structure of Formula (I) or cosmetically suitable salts thereof:

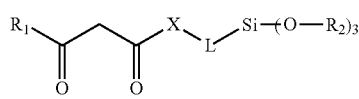

wherein $R_1$ is hydrogen or a $C_1$-$C_{20}$ hydrocarbon optionally substituted with 1-12 heteroatoms selected from oxygen, nitrogen, sulfur and halogen;

$R_2$ is independently selected at each occurrence from methyl, ethyl, propyl, butyl, pentyl, hexyl, phenyl or benzyl;

X is a bond, —O—, —$NR^N$—, or —S—; and

L is a group of the form —$X_1$—$(CR^*_2)_n$—$X_2$—$(CR^*_2)_m$—$X_3$—; wherein $X_1$, $X_2$, and $X_3$ are independently at each occurrence a bond, —O—, —$NR^N$—, —S—, —$(OCH_2CH_2)_y$—, or —$(CH_2CH_2O)_z$—, wherein y and z are independently an integer from 1 to 10, and n and m are independently an integer from 0 to 10;

$R^N$ is independently at each occurrence hydrogen, methyl, ethyl, propyl, butyl, pentyl, hexyl, phenyl or benzyl; and $R^*$ is independently selected at each occurrence from $C_1$-$C_4$ alkyl, hydrogen, or halogen;

wherein said benefit agent is in particulate form having a median particle size greater than about 5 nm; and (2) applying the functionalized benefit agent to a keratinous surface and allowing the benefit agent reversibly adhere thereto.

20. The method of claim 19, further comprising removing the benefit agent by contacting the keratinous surface having the benefit agent adhered thereto with an amine containing solution.

* * * * *